United States Patent [19]

Chess et al.

[11] Patent Number: 5,788,966
[45] Date of Patent: Aug. 4, 1998

[54] ANTIBODY WHICH IS DIRECTED AGAINST AND INHIBITS COLLAGEN BINDING TO A VLA-1 EPITOPE AND USES THEREOF

[75] Inventors: Leonard Chess, Scarsdale, N.Y.; Ilan Bank, Ramat-Hasharon, Israel

[73] Assignee: The Trustees of Columbia University in the City of New York, New York, N.Y.

[21] Appl. No.: 390,528

[22] Filed: Feb. 17, 1995

Related U.S. Application Data

[63] Continuation of Ser. No. 576,606, Aug. 31, 1990, Pat. No. 5,391,481.
[51] Int. Cl.[6] .................................................... A61K 39/395
[52] U.S. Cl. ..................... 424/144.1; 424/154.1; 424/173.1; 424/178.1; 424/183.1
[58] Field of Search .......................... 424/144.1, 154.1, 424/173.1, 178.1, 183.1; 530/391.7

[56] References Cited

U.S. PATENT DOCUMENTS 5,045,451   9/1991   Uhr et al. .............................. 435/7.23

OTHER PUBLICATIONS

P.A. Ward et al, Therapeutic Immunology, 1, 165–171, 1994.

*Primary Examiner*—David Saunders
*Attorney, Agent, or Firm*—John P. White

[57] ABSTRACT

The present invention provides methods of treating a subject suffering from a disorder associated with elevated levels of VLA-1 which comprises administering to the subject a therapeutically effective amount of an antibody which specifically forms a complex with VLA-1, inhibits collagen binding to VLA-1, and is directed to the epitope to which antibody 1B3.1 (ATCC No. HB10536) is directed and a pharmaceutically acceptable carrier.

14 Claims, 5 Drawing Sheets

ANTIBODY WHICH IS DIRECTED AGAINST AND INHIBITS COLLAGEN BINDING TO A VLA-1 EPITOPE AND USES THEREOF

This application is a continuation of U.S. Ser. No. 07/576,606, filed Aug. 31, 1990, now U.S. Pat. No. 5,391,481, issued Feb. 21, 1995, the contents of which are hereby incorporated by reference.

The invention described herein was made in the course of work under Grants Nos. GM 14969 and 24748 from the National Institute of Health. The U.S. Government has certain rights in this invention.

BACKGROUND OF THE INVENTION

Throughout this application, various publications are referenced by Arabic numerals with parentheses. Full citations for these publications may be found at the end of the specification immediately preceding the claims. The disclosures of these publications in their entireties are hereby incorporated by reference into this application in order to more fully describe the state of the art as known to those skilled therein.

Members of a protein complex called very late antigens (VLA) are expressed on the surface of T-cells (1–4). The VLA proteins constitute a family of six distinct heterodimers (VLA-1–6) that all share a common 110 kDa (non-reduced, MR) VLA subunits but differ in their α subunits which range in their molecular weights from 200 to 130 kDa (α1–α6) (5,25). Reportedly, the common β-subunit fibronectin and laminin and VLA-5 heterodimer has been found to be identical to the human fibronectin receptor (6).

The N-terminal sequences of the VLA α subunits are homologous to the α subunits of the LFA-1, Mac-1 (CR-3) and P 150/95 molecular family, as well as to the vitronectin receptor-platelet GP IIb/IIIa family, and a position-specific (PS) antigen important in Drosophila embryogenesis (7). Many of these molecules recognize ligands containing Arg-Gly-Asp sequences and are members of the supergene integrin family of adhesive protein receptors which have been highly conserved during evolution (8,9).

In long-term cultured T cells, the major VLA protein expressed are VLA-1 (200/110 kDa) and VLA-2 (165/110 kDa) (1,2). To a lesser intent, VLA-3 (150/110 kDa) is also expressed (5). The identification of these specific members of the VLA family was facilitated by the development of monoclonal antibodies (MoAbs) that specifically recognize each heterodimer (4,5,10).

A new monoclonal antibody (MoAb), 1B3.1, which reacts with a novel VLA-1 epitope is described herein. Since 1B3.1 was raised against T cells belonging to the Tγ lineage, our data surprisingly show that T cells of this lineage may also express receptors for cell matrix adhesion-related proteins, which may be of importance in the various functions of this subset of T cells.

Neils Odum, et al. (29) has described the increased prevalence of last stage T cell activation antigen or VLA-1 in active juvenile chronic arthritis. The increased prevalence was measured using a panel of MoAbs including a monoclonal antibody, anti-VLA-1 MoAb, TS2/7 (Coulter clone) (1) which specifically recognizes a molecular determinant, i.e. epitope, on the VLA-1 molecule or the VLA-1 protein.

MoAb TS2/7 recognizes a VLA-1 epitope distinct and separate from a VLA-1 epitope recognized by MoAb 1B3.1. An experiment was performed which accessed the ability of MoAbs 1B3.1 and TS2/7 to block the binding TS2/7 to VLA-1. 1B3.1 MoAb was unable to inhibit the binding of $^{125}$I- I-TF2/7 in this assay (FIG. 5). In contrast, unlabeled TS2/7 did inhibit the binding of the iodinated I-TF2/7. This result confirmed that MoAb TS2/7, but not IB3.1, was able to block FITC/conjugated TS2/7 stain of activated T cells. Accordingly, 1B3.1 and TS2/7 recognized non-overlapping epitopes of the VLA-1 molecule.

The subject antibodies provides the following advantages: a) a means to identify a previously unidentified epitope of the VLA-1 molecule, b) a means to identify a subset of T cells expressing VLA-1, c) a means to identify a subset of T cells associated with certain inflammation-related diseases and d) a means to elucidate in detail the structure and functions of the VLA-1 molecule in conjugation with other monoclonal antibodies which recognize an epitope on VLA-1.

SUMMARY OF THE INVENTION

The present invention provides an antibody which specifically forms a complex with VLA-1, inhibits collagen binding to VLA-1, and is directed to the epitope to which monoclonal antibody 1B3.1 (American Type Culture Collection (ATCC No. HB10336) is directed including methods of using same.

BRIEF DESCRIPTION OF THE INVENTION

FIG. 1: Graph showing the activities of MoAb 1B3.1 with activated T cells. CII (a), IBP2 (b), 235 (c), ID9 (d), and 4-PHA-activated T cell (e) where analyzed with an orthocytofluorograph. The first step reagents were; medium (1), MoAb WT31 (2) MoAb OKT3 (3), and MoAb 1B3.1 (4). The second step reagents was FITC. The Y axis is proportional to the number of cells and the X axis is proportional to the fluorescence intensity.

FIG. 2: Graph showing reactivity of monoclonal MoAb 1B3.1 with synovial T cells. PBMC (a) and synovial fluid mononuclear cells (b) from 2 patients were patients were analyzed on a Becton Dickinson FACS 440. The first step reagents were medium (1), OKT3 (2) and MoAb 1B3.1 (3). Results are shown in logarithmic scale.

FIG. 3: Immunological precipitation of IDP2 $^{125}$ I-labeled surface protein with MoAbs 1B3.1 and A1 A5. Cell extracts from $^{125I-labeled}$ IDP2 cells were immunoprecipitated as described under materials and methods using control antibody P3 (lane A), MoAb 1B3.1 (lane B), MoAb A1A5 (lane C). SDS —PAGE analysis shown in non-reducing conditions.

FIG. 4: A photograph of an SDS page gel showing a comparison of VLA protein with antigen precipitation by 1B3.1. And $^{125I}$ labeled extract and primary fibroblast cell line. GM3349 was either used directly (lanes 1-c), or precleared of all VLA-1 by three successive incubations with the MoAb TS2/7 (lanes D–S). The fibroblast extract was then used for immunoprecipitations by A1.A5 (VLA, lanes A, D,) TS2/7 (VLA-1, lane B, E) and by 1B3.1 (lanes C, F).

FIG. 5: Graph showing competitive inhibitions of binding of $^{125}$I-TS2/7 2 RD cells by unlabelled MoAbs cells 1B3.1, A1A5, and TS2/7 MoAb. The rhabdomyosarcoma cell line (RD at $1 \times 10^{-6}$ cells per well) plus preincubated with varying dilutions of the indicated MoAb and then after washing was tested for binding by $I^{125}$-TS2/7.

DETAILED DESCRIPTION OF THE INVENTION

Figure 1:
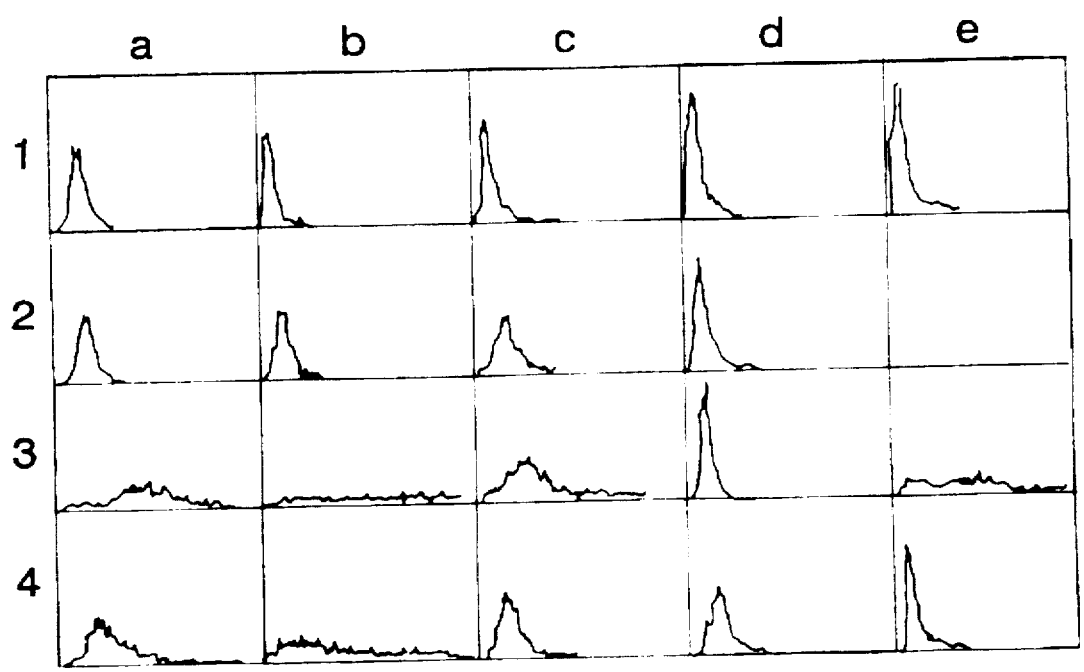

The present invention provides an antibody which specifically forms a complex with VLA-1, inhibits collagen binding to VLA-1, and is directed to the epitope to which monoclonal antibody 1B3.1 (ATCC No. HB10336) is directed. Additionally, this invention provides the monoclonal antibody 1B3.1 (ATCC No. HB10536).

This invention encompasses any immunologically reactive or active fragment or molecule which recognizes the epitope to which monoclonal 1B3.1 (ATCC No. HB10536) is directed since it would be clear to those ordinarily skilled in the art that these fragments or molecules would be a functional equivalent of the claimed antibodies.

Further, in one embodiment of the invention the above-described antibodies may be a monoclonal antibody. Alternatively, in another embodiment, the above-described antibodies may be a polyclonal antibody. A monoclonal antibody is preferred.

Additionally, in one example, the monoclonal antibody is desginated 1B3.1 (ATCC No. HB10536). 1B3.1 is produced by the hybridoma 1B3.1 (ATCC No. HB10536). The hybridoma that produces 1B3.1 is designated 1B3.1 hybridoma. The 1B3.1 hybridoma has been deposited pursuant to the Budapest Treaty On the International Recognition Of The Deposit of Microorganisms For The Purposes of Patent Procedure with the Patent Culture Depository of the American Type Culture Collection, 12301 Parklawn Drive, Rockville, Md. 20852 U.S.A. under (ATCC No. HB10536). The present invention further provides a monoclonal antibody produced by the VLA-1 hybridoma.

In accordance with the practice of this invention, the previously-described antibodies, e.g. 1B3.1, may be labeled with a detectable marker. Examples of suitable detectable marker includes, but are not limited to, an enzyme, a paramagnetic isotope, biotin, a fluorophore, a chromophore, a heavy metal, or a radioisotope. By suitable detectable marker, applicants contemplate any label which would be conducive to the detection of a complex which are known in the art.

For example, it would be clear to those skilled in the art that one method of attaching the subject antibody to an enzyme would be by a modification of the periodate method (28). Alternatively, it would be clear to those skilled in the art to attach a ligand to the subject antibodies and a receptor of the ligand to the enzyme. A suitable ligand receptor combination is biotin-avidin in accordance with the method of Bayer et al. (27).

Additionally, the present invention provides a method of detecting VLA-1 in tissue sections which comprises contacting the tissue sections with any of the antibodies described above under conditions such that the antibody binds to the tissue sections and detecting the antibody bound to the tissue sections and thereby detecting VLA-1 in the tissue sections. In one example, the tissue is muscle tissue. Alternatively, in another example, the tissue is epithelial tissue (such as gut epithelial tissue). In yet another example, the tissue is a connective tissue (such as blood, joint connective tissue, or cartilage).

In one embodiment of the above-described method, the antibody is labeled with a detectable marker. Suitable detectable markers include, but are not limited to, enzymes, biotin, fluorophores, chromophores, heavy metals, paramagnetic isotopes, or radioisotopes.

This invention also provides a method for determining a difference in the amount and distribution of VLA-1 in tissue sections from a diseased tissue (diseases such as rheumatoid arthritis and other tissue-inflammation associated diseases) to be tested relative to the amount and distribution of VLA-1 in tissue sections from a normal tissue. This method comprises contacting both the tissue to be tested and the normal tissue with the above-described antibodies, i.e. 1B3.1, and thereby detecting the difference in the amount and distribution of VLA-1.

Additionally, the invention provides a method for determining a difference in the amount and distribution of VLA-1 in a biological fluid sample to be tested relative to the amount of VLA-1 in a biological fluid sample from a normal subject which comprises contacting both the biological fluid sample to be tested and the biological fluid sample from the normal subject with any of the previously-identified antibodies, e.g. 1B3.1, and thereby detecting the difference in the amount of VLA-1 in the samples. In one example, the antibody is directed to the epitope to which monoclonal antibody 1B3.1 (ATCC No. ) is directed. Further, in one example of the above-described method, the tissue is muscle tissue. Alternatively, in another example, the tissue is epithelial tissue (such as gut epithelial tissue). In yet another example, the tissue is a connective tissue (such as blood, joint tissue or cartilage).

Further, in accordance with the practice of this invention, the biological fluid may be selected from a group consisting of spinal fluid, synovial fluid, tissue extract, urine, blood, serum, and phlegm.

This invention further provides a method for detecting denatured VLA-1 in a sample (for example a biological fluid or tissue sample). The method comprises contacting the sample with any of the labeled antibodies described hereinabove (e.g. 1B3.1) such that the VLA-1 binds to the antibody (preferably a monoclonal antibody) and forms a complex therewith; and detecting such complex.

In one example of the method, the sample containing VLA-1 is transfered onto a suitable support under conditions permitting VLA-1 in the sample to attach to the support prior to contacting the sample with labeled antibody. Examples of suitable sample include, but are not limited to, synovial fluid, serum, urine, blood, a tissue extract, or phlegm.

Additionally, this invention further provides a method for diagnosing a disorder associated with elevated levels of VLA-1 in a subject. This method comprises obtaining from the subject a volume of biological fluid and detecting VLA-1 in such bodily fluid using the method for detecting denatured VLA-1 in a sample; thereby diagnosing such condition.

Additionally, this invention provides a method for detecting and quantitatively determining the concentration of VLA-1 in a biological fluid sample. This method comprises: (a) contacting a solid support with an excess of any of the previously-described antibodies, e.g. 1B3.1, under conditions permitting the antibody to attach to the surface of the solid support; (b) contacting the resulting solid support to which the antibody is bound with a biological fluid sample under conditions such that the VLA-1 in the biological fluid binds to the antibody and forms a complex therewith; (c) contacting the complex formed in step (b) with a predetermined amount of a second antibody labeled with a detectable marker and directed to an epitope on VLA-1 different from the epitope to which the antibodies of step (a) is directed, so as to form a complex which includes VLA-1, the antibody, and the second detectable antibody; (d) detecting and quantitatively determining the concentration of second detectable antibody present in the complex formed in step (c); and (e) detecting and quantitatively determining the concentration of VLA-1 in the biological fluid sample.

In one example of the above-described method, the antibody bound to the solid support is directed to the epitope to which monoclonal antibody 1B3.1 (ATCC No. HB10536) is directed. Further, in another example, the second antibody is directed to the epitope to which monoclonal antibody TS2/7 (1) is directed. Additionally, in accordance with the invention, the biological fluid may be selected from a group consisting of spinal fliud, synovial fluid, tissue extract, urine, blood, serum, and phlegm.

Also, in step (c) of the above-described method, the detectable marker attached to the second antibody may be an enzyme, biotin, a fluorophore, a chromophore, a heavy metal, a paramagnetic isotope, or a radioisotope.

Further, this invention provides a method of treating a subject suffering from a disorder associated with elevated levels of VLA-1. This method comprises administering to the subject an effective amount of any of the antibodies (e.g. 1B3.1) and a pharmaceutically acceptable carrier. In one example, administration comprises intravenous administration.

In the methods described herein, it would be clear to those skilled in the art that the subject may be a human subject, or other animals including pigs, cows, dogs, birds, sheep, and cats.

Those skilled in the art will readily appreciate that amounts effective to reduce the level or concentration of (1) circulating VLA-1 in a human being's biological fluids or (2) on the cell surface of T cells may be readily determined and that any of the conventional pharmaceutically acceptable carriers useful for administering an antibody may be employed such as sterile saline or buffers, liposomal formulations, and the like.

Further, examples of suitable carriers are well known in the art and may include, but are in no way and are not intended to be limited to, any of the standard pharmaceutical carriers such as a phosphate buffered saline solutions, water, emulsions such as oil/water emulsion, and various types of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

The present invention also provides a method for inhibiting collagen binding to VLA-1 which comprises treating the cells with an amount of any of the previously-described antibodies (e.g. 1B3.1).

Further, the present invention provides a method for inhibiting the biological activity of VLA-1 which comprises contacting VLA-1 with an amount of any of the antibodies, e.g. 1B3.1, effective to inhibit the activity of VLA-1.

Additionally, this invention provides a composition which comprises any of the above described antibodies, e.g. 1B3.1, to which an imaging agent is attached. Examples of suitable imaging agents include, but are not limited to, a paramagnetic isotope, a heavy metal, or a radioisotope.

Further, this invention provides a therapeutic composition which comprises any of the previously-described antibodies, e.g. 1B3.1, to which a therapeutic agent is attached. Such a therapeutic agent include, but is not limited to, a toxin selected from a group consisting of ricin, diphtheria toxin, pseudomonas, exotoxin-A, abrin, supporin, and gelonin. Other therapeutic agents includes drugs and other disease controlling agents whether synthetically or naturally derived.

Finally, the invention also provides a therapeutic method. The method comprises administering to a subject an effective amount of the above-described therapeutic composition.

This invention is illustrated in the Experimental Details section which follows. This section is set forth to aid an understand of the invention but is not intended to, and should not be construed to, limit in any way the invention as set forth in the claims which follow.

EXAMPLE 1

MATERIALS AND METHODS

Lymphoid Cell Subpopulations and Derivation of Activated T Cells and Clones.

Peripheral blood mononuclear cells (PBMC) thymocytes and synovial lymphocytes were obtained by Ficoll-Hypaque density centrifugation, as previously described, and $E^+$ (T) and $E^-$ cells were separated on the basis of rosetting with sheep red blood cells (SRBC) (11, 12). Thymocytes were obtained from thymic tissue removed from children undergoing cardiac surgery. The thymocyte subpopulations ($CD4^-$, $CD8^-$) and $CD1^-$ were obtained by a process of negative selection using MoAbs OKT4, OKT8, and OKT6 (Ortho, Raritan, NJ) followed by resetting of the antibody-treated cells with ox red blood cells coupled to rabbit anti-mouse IgG, as previously described (12). PHA-activated T cells and cloned T cell lines were cultured in Iscoves modified Dulbecco's medium (IMDM) (GIBCO) supplemented with 10% FCS, 1% penicillin-streptomycin (Sigma), recombinant interleukin-2 (IL-2), and 1% glutamine (Sigma) as previously described (12).

Antibodies and Cell Lines.

MoAb OKT3 (anti-CD3) obtained from Ortho (Raritan, NJ) MoAb WT31 (anti-T cell receptor $\alpha\beta$), and MoAb UCHTI (anti-CD3) were used (13). The CII and IDP2 IL-2-dependent cell lines express a CD3-associated T cell receptor (TCR) encoded by the T$\gamma$ and T$\delta$ genes, and have been previously described in detail (12,13). The cloned 252 thymocyte cell line ($CD3^-$ $WT31^+$ $CD4^+$) was derived from a CD1-thymocyte population. The $CD3^-$ $WT31^-$ clone ID9 was grown in IL-2 from a $CD4^-$ and $CD8^-$ thymocyte population. Lymphoblastoid B cell lines (LBCL) and the continuously growing PEER, RPMI 8402, HPB MLT, and U937 cell lines were grown in RPMI or IMDM medium with 10% FCS. The primary fibroblast cell line Gm3349 and rhabdomyosarcoma cell line RD were grown in $\alpha$ medium and 10% FCS (5).

Hybridoma Production

CII cells were used to immunize Balb/c mice, and mouse spleen cells were fused with the myeloma NS-1 line as previously described (14). The IB3 hybridoma was selected for reactivity with CII cells by cytofluorographic analysis and was cloned at limiting dilutions. Undiluted supernatants of IB3.1 hybridoma (IgA), or ascites fluid (1:2000 final dilution) obtained from pristane-treated Balb/c mice injected intraperitoneally with the IB3.1 clone as indicated in the text.

Labeling and Immunoprecipitation of Cell Surface Proteins

Nonadherent cells were radioiodinated by the immunoperoxidase technique as previously described (13). Briefly, labeled cells were lysed in 5 ml of TBS (10 mM Tris pH8, 14 mM NaCl) with 0.8 3-[3-cholamidopropylidmethylammonio]-1 propane sulfonate (CHAPS), which preserves the TCR-CD3 association, containing 2 mM phenyl methylsulfonyl fluoride (PMSF) and 5 mM iodoacetamide (IAA). Immunoprecipitation was carried out using fixed Staphylococcus aureus Cowan I as previously described, and the immune complexes were washed five times on TBS containing 0.1% Triton x-100 (Tx-100) (13). Reduced samples were boiled in 2 mM dithiothreitol (DTT), and all samples incubated for 10 min. at 23° C. in 10 mM IAA before analysis by SDS-PAGE. Cell surface proteins on adherent cells were labeled with $^{125}$I (1 Mc/$10^7$ cells), using lactoperoxidase, while the cells were still attached, as previously described (5).

Fluorescent Staining and Flow Cytometry

Cells (1–10×$10^6$) were pelleted, resuspended, and incubated in the presence of the indicated MoAb for 30 min at room temperature, followed by two washes in PBS containing 1% BSA and 0.02% azide. The washed cells were then incubated with 10% of fluorescein isothiocyanate (FITC)-conjugated F(ab')$_2$ derivative of goat anti-mouse IgG heavy and light chain (Cappel Laboratories) for 30 min at 4° C., in the dark. The cells were washed again three times and $10^3$ cells were analyzed on an Ortho cytofluorograph. In the clinical studies cells were analyzed on a FACS-440 (Becton-Dickinson). Results from the patient material are shown in the logarithmic scale.

Patients

Patients from the Arthritis Clinic at the Sheba Medical Center. We present data from specimens derived from two patients who had knee effusions of >3 weeks duration. The synovial fluid was removed for clinical indications. These studies were approved by the Helsinki Committee at the Sheba Medical Center.

RESULTS

Preparation and Tissue Distribution of MoAb 1B3.1

Balb/c mice were immunized with intact CD3+ Tγδ+ CII cells (12), and the immune splenocytes were fused with the NS-1 myeloma cell line. The resulting hybridoma supernatants were screened by cytofluorography for their reactivity with CII cells, but not with feeder cells in the CII cultures or with resting T cells. The supernatants of one clone, IB3.1, reacted with CII cells, and with other long-term IL2-dependent T cells of CD3−, CD3+Tγδ and CD3+Tαβ lineage, but not with resting T cells that had been activated for 4 days with PHA (FIG. 1), IB3.1 also did not react with the PEER, HPBMLT, or Molt4 T cell lines, but showed low-level reactivity with the RPMI 8401 T cell line. No reactivity was detected in resting B cells or macrophages, on the U937 cell line, or on the majority of LBCL.

Figure 2:
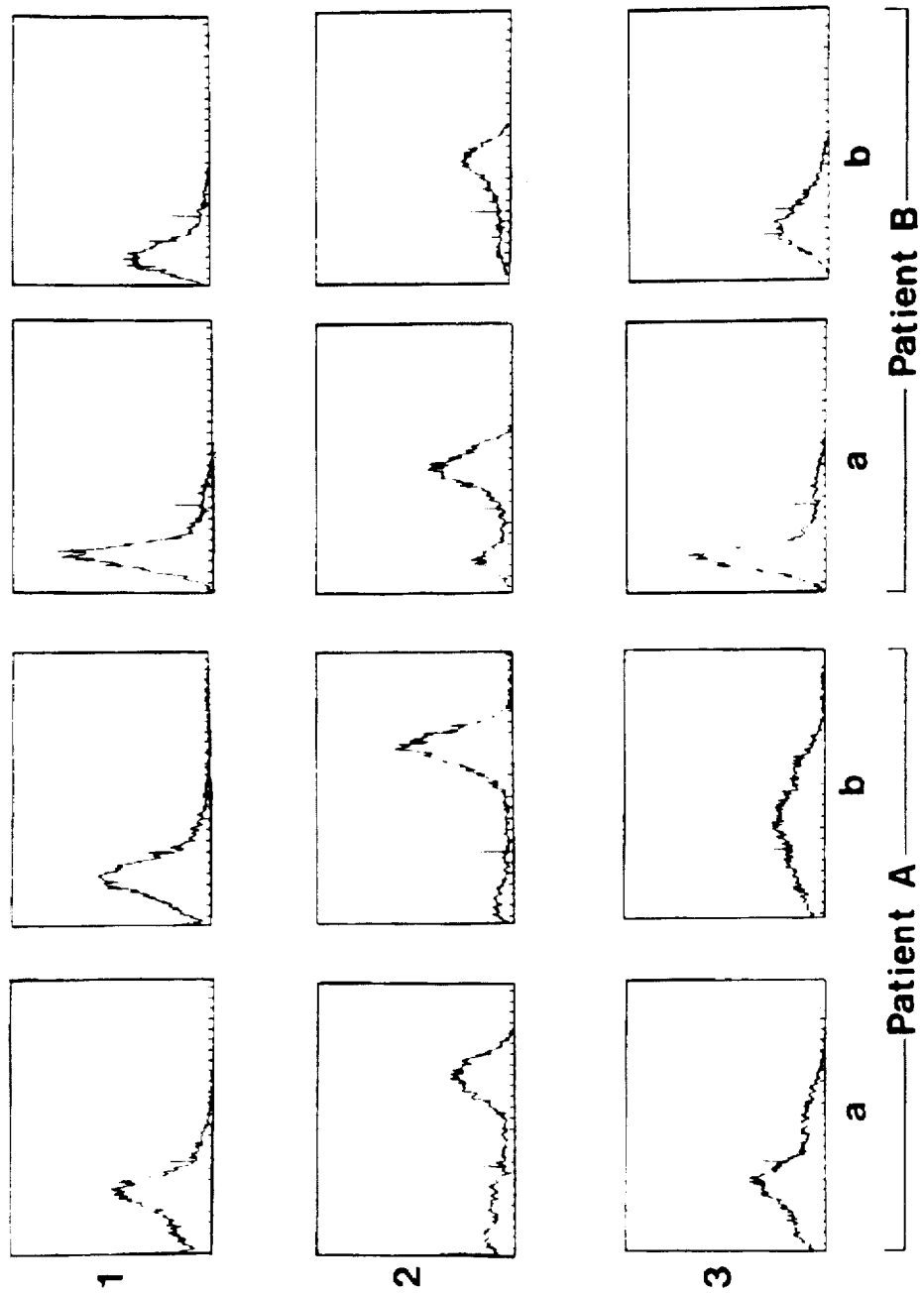

Since these data suggested that 1B3.1 reacts with long term stimulated T cells, we also assessed its reactivity with activated T cells from synovial fluid of several patients with chronic synovitis. As shown in FIG. 2, 1B3.1 staining of the synovial T cells was greater than the staining of simultaneously drawn PBMC.

Taken together these data demonstrate that MoAb 1B3.1 reacts with T cells which have been activated for prolonged periods, both in vitro and in vivo.

Identification of 1B3.1 Target Antigens

Figure 3:
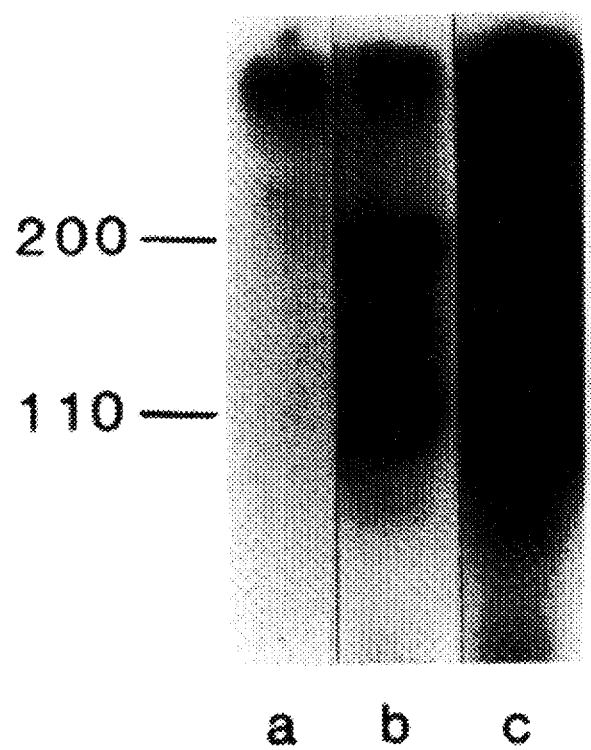
Figure 4:
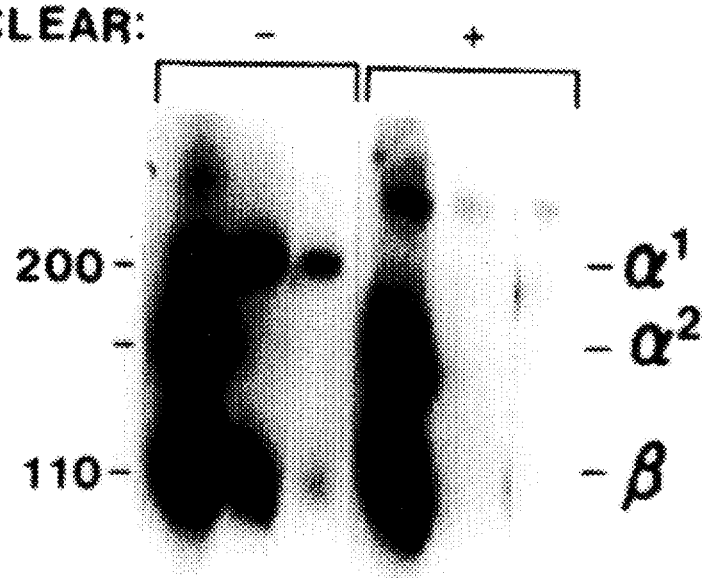

To identify the target antigens of MoAb 1B3.1, $^{125}$I-labeled cell surface proteins of the IDP2 cell line were immunoprecipitated with MoAb 1B3.1 supernatants and analyzed by SDS-PAGE. As shown in FIG. 3, lane b, under non-reducing conditions, 1B3.1 precipitated two major bands of 200 and 110 kDA, and a weaker 150 kDa band similar in size to proteins of the VLA family. Thus, as shown in FIG. 3, lane c, MoAb A1A5 (anti-VLA-β) precipitated high Mr. peptides of 200, 165, and 110 kDa, corresponding to the VLA-α1, -α2, and VIA-β chains from the IDP2 lysates (4,5). These data were extended in studies in which $^{125}$I-labeled surface proteins from normal fibroblasts were immunoprecipitated using the MoAbs A1A5 (anti-VLA-β), TS2/7 (specific for VLA-1), and 1B3.1 (FIG. 4) (1,4). As expected, MoAb A1A5 precipitated proteins of Mr 210, 165, and 110 kDa corresponding to the VLA α1, α2, and VLA-β subunits, respectively (FIG. 4, lane a) (5). MoAb TS2/7 precipitated a single 200-kDA α1 subunit, and the common 110kDa β subunit (FIG. 4, lane b). MoAb 1B3.1 also precipitated 200 and 110-kDa bands from the surface of the iodinated fibroblasts (FIG. 4, lane c). These results further suggested that 1B3.1 is directed against VLA-1 heterodimers.

To confirm that MoAb 1B3.1 recognizes VLA-1 proteins, the fibroblast lysates were precleared with MoAb TS2/7, and the precleared material was immunoprecipitated with MoAbs A1A5, 1B3.1, and TS2/7. After preclearing MoAb TS2/7 did not precipitate any material, indicating that the preclearing of VLA-I heterodimers had been complete (FIG. 4, lane e). MoAb 1B3.1 also failed to precipitate either the 200- or the 110-kDa subunits (FIG. 4, lane f), and MoAb A1A5 precipitated only the 165-kDa α2 subunit and the 110-kDa β subunit. These results show that MoAb Ib3.1 and TS2/7 both recognize the VLA-1 heterodimer. Furthermore, cytofluorographic analysis of activated T cells revealed identical staining when saturating amounts of the two MoAbs were used.

Figure 5:
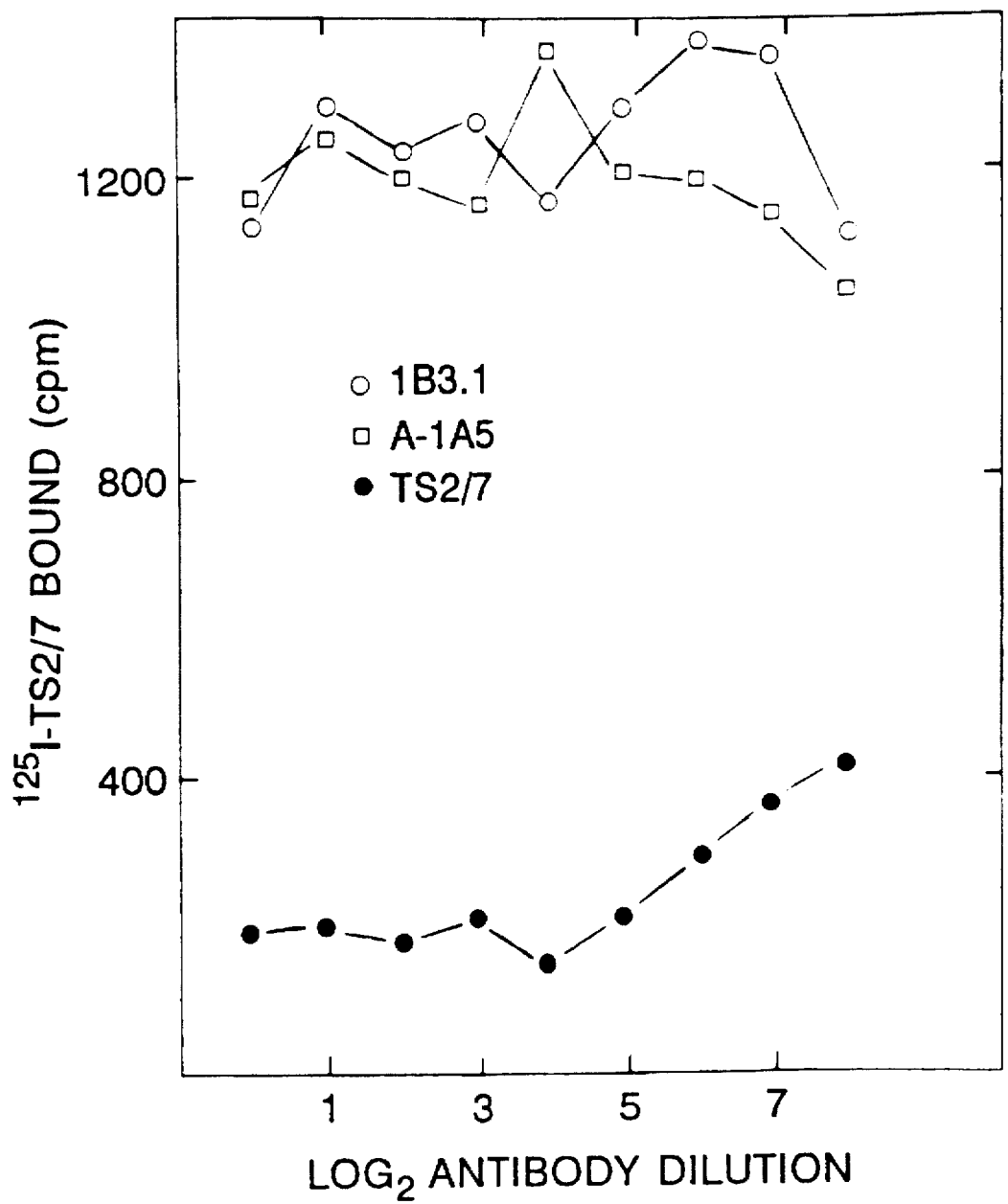

To determine whether TS2/7 and 1B3.1 recognize the same VLA-1 epitopes, the ability of MoAbs 1B3.1, TS2/7, and AIA5 to block the binding of TS2/7 to VLA-1 was assessed. Neither A1A5 nor 1B3.1 antibodies were able to inhibit the binding of $^{125}$I-TS2/7 in this assay (FIG. 5). In contrast, "cold" TS2/7 did inhibit the binding of the iodinated antibody. These results were confirmed in experiments in which MoAb TS2/7, but not 1B3.1, was able to block FITC-conjugated TS2/7 staining of activated T cells. Thus, 1B3.1 and TS2/7 recognize nonoverlapping epitopes of the VLA-1 molecule.

DISCUSSION

This paper describes a new MoAb, 1B3.1, that reacts with long term activated T cell lines but not with resting or short-term activated T cells. The target antigen of MoAb 1B3.1 consists of proteins of 200 and 110 kDa that are identical to VLA-1 proteins. MoAb 1B3.1 binds to a novel epitope of the VLA-1 protein which is distinct from the binding site of the previously described anti-VLA-1 MoAb, TS2/7 (FIG. 5) (1).

The availability of MoAbs directed against noncompeting VLA-1 epitopes will be useful in future studies of the functions of the VLA-1 molecule, as has been the case in studies of molecules such as CD4 and CD2 (15, 16). In the latter example, MoAbs have allowed definition of binding and activating sites (16). Although no specific function has as yet been assigned to VLA-1, it is likely that this molecule is involved in the binding of extracellular matrix materials, since other members of the VLA family have already been shown to be receptors for collagen (VLA-2 and VLA-3, laminin (VLA-3), and fibronectin (VLA-3 and VLA-5) (9). If VLA-1 is matrix receptor, MoAb 1B3.1 and MoAb TS2/7 will helpful in defining its substrate specificity, the molecular domains involved in the interactions of VLA-1 with its ligand and the functional consequences of these interactions. Preliminary experiments in our laboratory suggest that binding of the 1B3.1 epitope can regulate T cell proliferation.

It has already been shown that T lymphocytes residing in the normal lung, the spinal fluid of multiple sclerosis patients, and the synovial fluid of arthritis patients, express enhanced levels of VLA-1(17–19). Since molecules of the integrin super family have been previously shown to play a role in the thymic colonization by hematopoietic precursor cells, it is possible that the VLA-1 molecule participates in the compartmentalization of activated T cells to sites of tissue localized immune responses such as those occurring in synovia (9,20). Recent findings that the VLA-4 α chain is a homing receptor support this possibility (26).

Our studies show, for the first time that VLA-1 molecules can be expressed on cells of the Tγδ lineage. The immunoprecipitations using the IDP2 T γδ cell line revealed a weak 150-kDa peptide in addition to the 200/110-kDa peptides, that has not been previously described in VLA-1 precipitations of Tαβ cells. Since MoAb 1B3.1 did not precipitate a 150-kDa band in the fibroblast experiments, and further experiments have failed to precipitate the 150-kDa material in Tγδ or Tαβ clones, it is possible that this band represents a breakdown product of the 200-kDa α1 peptide in the IDP2 lysates. Since, there is no clear-cut evidence for significant differences between VLA-1 molecules on Tγδ and Tαβ cells.

Since Tγδ cells, like Tαβ cells can also express VLA-1, it is possible that some of VLA-1+ cells seen in lung tissue, synovial fluid, and spinal fluid are Tγδ expressing cells. Already some clones of T cells derived from spinal fluid have been shown to be Tγδ, and received data indicate Tγδ cells in inflamed joints (21, 22). In addition, Tγδ cells are found in the normal skin and in gut epithelium (23, 24). It is possible that the high levels of VLA-1 which are expressed on these cells play a role in their tissue localization.

In summary we have presented data concerning a new MoAb, 1B3.1 defining a novel epitope on the VLA-1 heterodimer. This MoAb will be useful in further studies of the structure and function of the VLA-1 molecule and of the cells expressing this structure.

In an experiment which determined the differences between TS2/7 and the subject monoclonal antibodies, with regard to the functional effect exerted on various cell lines due to binding as VLA-1 or TS2/7 clearly shows that claimed subject monoclonal antibodies exerted an effect on the cell lines which produced a functional effect different from that induced when TS2/7 was contacted with the same cell line.

REFERENCES

1. Hemler, M.E. et al. J. Biol. Chem. 260, 15246, 1985.
2. Hemler, M.E. and Jacobson, J.G., J.Immunol. 138(9), 2941, 1987.
3. Hemler, M.E. et al. J. Immunol 131, 334, 1983.
4. Hemler, M.E. et al. J. Immunol, 132, 3011, 1984.
5. Hemier, M.E. et al. J. Biol. Chem 262(7), 3300, 1987.
6. Takada, Y. et al. Nature (London) 326, 607, 1987.
7. Takada, Y. et al. Proc. Natl. Acad. Sci. U.S.A 84(10), 3239, 1987.
8. Hynes, R.O. cell 48, 549, 1987.
9. Hemier, M.E. Immuno. Today 9(4), 109, 1988.
10. Pischel. K.D. et al. J. Immunol. 138, 226, 1986.
11. Bank. I. and Chess L., J. Exp. Med. 162, 1294, 1985.
12. Bank. L et al. Nature (London) 322, 179, 1986.
13. Brenner, M.B. et al. Nature (London 322, 145, 1986.
14. Irigoyen, O.H. et al. Proc. Natl. Acad. Sci. U.S.A 78, 3160, 1981.
15. Rogozinski, L. et al. J. Immunol. 132(2), 735, 1984.
16. Springer, T.A. et al. Annu. Rev. Immuno. 5, 223, 1987.
17. Saltin, C. et al. Clin. Immunol. Immunopathol. 46(2), 221, 1988.
18. Hemler, M.E. et al. J. Clin. Invest 78, 696, 1986.
19. Hafler, D.A. et al. Clin. Immunol. Immunophathol., 37, 163, 1985.
20. Savagner, P. et al. J. Cell Biol. 103, 2715, 1986.
21. Demaria, A. et al. Eur. J. Immunol. 17, 1815, 1987.
22. Borst, J. et al. Nature (London) 325, 683, 1987.
23. Goodman, T. and Lefrancois, L., Nature (London) 333, 855, 1988.
24. Koning, F. et al. Science 236, 834, 1987.
25. Hemler, M.E. et al. J. Biol. Chem. 263, 7660, 1988.
26. Holzman, B. et al. Cell 56, 37, 1989.
27. Wilson, M.B. and Nakane, P.K. (1978) Immunofluorescence and Related Staining Techniques (Elsevier/North Holland Biomedical Press, Amsterdam) 215.
28. Bayer et al. (1979) Methods in Enzymology, 62:308.
29. Neils Odum et al. Annals of the Rheumatic Diseases 46: 846–852, 1987.

What is claimed is:

1. A method of treating a subject suffering from a disorder associated with elevated levels of VLA-1 which comprises administering to the subject a therapeutically effective amount of an antibody which specifically forms a complex with VLA-1, inhibits collagen binding to VLA-1, and is directed to the epitope to which antibody 1B3.1 (ATCC No. HB10536) is directed and a pharmaceutically acceptable carrier.

2. A method of claim 1, wherein the antibody is monoclonal.

3. A method of claim 1, wherein the antibody is polyclonal.

4. A method of claim 2, wherein the monoclonal antibody is designated 1B3.1 (ATCC No. HB10536).

5. A method of claim 1, wherein administration comprises intravenous administration.

6. A method of claim 1, wherein the subject is a human being.

7. A method for inhibiting collagen binding to VLA-1 which comprises treating cells with a therapeutically effective amount of an antibody which specifically forms a complex with VLA-1, inhibits collagen binding to VLA-1, and is directed to the epitope to which antibody 1B3.1 (ATCC No. HB10536) is directed.

8. A method for inhibiting activity of VLA-1 which comprises contacting VLA-1 with an amount of an antibody which specifically forms a complex with VLA-1, inhibits collagen binding to VLA-1, and is directed to the epitope to which antibody 1B3.1 (ATCC No. HB10536) is directed effective to inhibit the activity of VLA-1.

9. A therapeutic composition which comprises an antibody or a portion thereof which specifically forms a complex with VLA-1, inhibits collagen binding to VLA-1, and is directed to the epitope to which antibody 1B3.1 (ATCC No. HB10536) is directed to which a therapeutic agent is attached.

10. A therapeutic composition of claim 9, wherein the antibody is monoclonal.

11. A therapeutic composition of claim 9, wherein the antibody is polyclonal.

12. A therapeutic composition of claim 10, wherein the monoclonal antibody is designated 1B3.1 (ATCC No. HB10536).

13. A therapeutic composition of claim 9, wherein the therapeutic agent comprises a toxin selected from the group consisting of ricin, diphtheria toxin, pseudomonas, exotoxin-A, abrin, supporin, and gelonin.

14. A therapeutic method which comprises administering to a subject a therapeutically effective amount of the therapeutic composition of claim 13.

* * * * *